United States Patent
Bernicot et al.

[11] Patent Number: 5,661,248
[45] Date of Patent: Aug. 26, 1997

[54] METHOD AND APPARATUS FOR NON-INTRUSIVE MEASUREMENT AND CONTROL OF THE FLOW RATES OF THE DIFFERENT PHASES OF A MULTIPHASE FLUID IN A PIPELINE

[75] Inventors: Michel Bernicot, Saint Germain en Laye; Thierry Romanet, Marseilles, both of France

[73] Assignees: Total, Puteaux; Syminex, Marseilles Cedex, both of France

[21] Appl. No.: 404,567

[22] Filed: Mar. 15, 1995

[30] Foreign Application Priority Data

Mar. 15, 1994 [FR] France .................. 94 02981

[51] Int. Cl.$^6$ .................................................. G01F 1/74
[52] U.S. Cl. .................................................. 73/861.04
[58] Field of Search .................. 73/861.04, 861.27, 73/61.45; 137/558

[56] References Cited

U.S. PATENT DOCUMENTS

| | | | |
|---|---|---|---|
| 3,140,701 | 7/1964 | Cooper et al. | 123/120 |
| 3,705,626 | 12/1972 | Glenn, Jr. et al. | 166/267 |
| 3,753,656 | 8/1973 | Matson et al. | 23/232 E |
| 4,329,880 | 5/1982 | Herzl | 73/861.24 |
| 4,348,906 | 9/1982 | Feller | 73/861.77 |
| 4,429,581 | 2/1984 | Furmaga | 73/861.04 |
| 4,628,725 | 12/1986 | Gouilloud et al. | 73/861.27 |
| 5,211,842 | 5/1993 | Tuss et al. | 73/861.04 |
| 5,218,871 | 6/1993 | Cody et al. | 73/861.04 |

FOREIGN PATENT DOCUMENTS

| | | |
|---|---|---|
| 0465032 | 1/1992 | European Pat. Off. . |
| 8905974 | 6/1989 | WIPO . |
| 9314382 | 7/1993 | WIPO . |
| 9324811 | 12/1993 | WIPO . |

Primary Examiner—Richard Chilcot
Assistant Examiner—Jewel V. Artis
Attorney, Agent, or Firm—Sughrue, Mion, Zinn, Macpeak & Seas

[57] ABSTRACT

A mechanical or acoustic excitation apparatus 26 imparts mechanical vibrations to a pipeline 12 in at least two longitudinally spaced areas of its outer surface. At least one sensor 30 is positioned in proximity to the pipeline, which collects vibration data supplied to it along the pipeline. A processing and analysis apparatus 40 derives from the vibration data information concerning the gas and liquid content of the multiphase fluid, in particular the length and rate of travel of liquid plugs and air pockets, and a control device 42 regulates intake valves of downstream petroleum equipment to adjust the intake flow rate of the phases as a function of the storage and/or treatment capacity of the equipment.

3 Claims, 2 Drawing Sheets

METHOD AND APPARATUS FOR NON-INTRUSIVE MEASUREMENT AND CONTROL OF THE FLOW RATES OF THE DIFFERENT PHASES OF A MULTIPHASE FLUID IN A PIPELINE

BACKGROUND OF THE INVENTION

This invention concerns the field of protection of hydrocarbon-production equipment, and, in particular, equipment located downstream from submarine well heads and/or equipment located on off-shore platforms (manned or unmanned).

The effluents collected at the outlet of an oil well are normally of the multiphase type; that is, they contain a mixture of gas, liquid, and potentially, solids. The effluents are circulated through a pipeline either to facilities on the coastline or to a treatment platform. Because of the instability of the multiphase flows, liquid plugs and/or gas pockets of fairly significant lengths inevitably form inside the pipelines. At the end of the pipeline, the transported fluid enters a separation tank, in which natural decantation of the multiphase fluid into its different phases is carried out. The liquid phase is extracted from the bottom of the tank and transported to separation and treatment equipment, while the gaseous phase is removed at the upper part of the tank and is treated and compressed before being used locally or shipped.

Patent No. EP-0 465 032 discloses a non-intrusive measurement system used to monitor flows of multiphase fluids containing plugs in a pipeline. However, in this system no active excitation of the pipeline is carried out, but rather, using external sensors, noise generated directly by the passage of the plugs in the pipeline is passively monitored. Moreover, this system incorporates no control means making it possible to regulate the intake valves of the equipment used to treat the gaseous and liquid phases.

Patent No. WO-A-89 05974 concerns a system for analyzing the composition of a multiphase fluid circulating in a pipeline. However, this system includes intrusive means for generating turbulence or cavitation noise in the fluid, in particular an impact valve. In addition, it does not incorporate mechanisms for controlling the intake valves in the treatment equipment. Patent No. WO-A-93 14382 raises the same problems.

Patent WO-A-93 24811 relates to a non-intrusive system for measurement of gas, oil, and water mass flow rates in multiphase flows containing plugs. Excitation is not, however, generated by a mechanical or acoustic excitation apparatus, but by a radioactive gamma ray source.

SUMMARY OF THE INVENTION

This invention determines the flow rates of the liquid and gas flowing through the pipeline by measuring the length and rate of travel of the plugs and pockets. Knowledge of the characteristics of the plugs and pockets makes it possible, by means of suitable regulation:

a) to prevent large gas pockets from reaching the separation tank, which would otherwise require channeling the excess gas to the surplus gas burners, where it would be burned as a total loss;

b) to maintain a relatively stable liquid phase level in the separation tank and, accordingly, to avoid clogging it as a result of the penetration of a long liquid plug; and c) to optimize the dimensions of the tank and the treatment equipment which, until now, had to be oversized to absorb pronounced effluent fluctuations.

The invention concerns a method for the non-intrusive measurement and control of the flow rates of the gaseous and liquid phases in a multiphase fluid circulating in a pipeline, for example between an oil well and a separation tank in which these gaseous and liquid phases are separated, and then transported to respective treatment equipment. The method is characterized by:

1) mechanically exciting the pipeline and the multiphase fluid it contains, by generating a vibratory or acoustic excitation in at least two areas of the outer surface of the pipeline upstream from the separation tank, each excited area being a measurement area, 2) recording the mechanical vibrations transmitted through the pipeline at at least one point lying outside the pipeline for each measurement area, 3) processing the vibrations and analyzing them in order to produce therefrom data concerning the presence of gas pockets and/or fluid plugs in the multiphase fluid, and the length and speed of travel of the liquid plugs and gas pockets, and 4) based on this information, controlling the flow rates at which the gaseous and liquid phases enter respective treatment equipment, in order not to exceed their treatment or storage capacities.

The invention also concerns an apparatus for implementing the method, and is characterized by:

i) one mechanical or acoustic excitation apparatus for each measurement area placed on the outside of the pipeline, upstream from the separation tank, for generating mechanical vibrations in at least two areas of its outer surface, ii) at least one sensor per measurement area, positioned in proximity to, and to the outside of, the pipeline and capable of collecting vibration and/or acoustic data transmitted to it from the excitation apparatus through the pipeline, iii) processing and analysis equipment which, based on the vibration data, produces information concerning the gas and liquid content (oil and water) of the multiphase fluid, and the length and speed of travel of the liquid plugs and air pockets, and iv) a control device for controlling the intake valves of the petroleum equipment, in order to adjust the intake flow rate of the phases as a function of the storage or treatment capacity of the equipment.

DETAILED DESCRIPTION OF THE PREFERRED EMBODIMENTS

Figure 1:
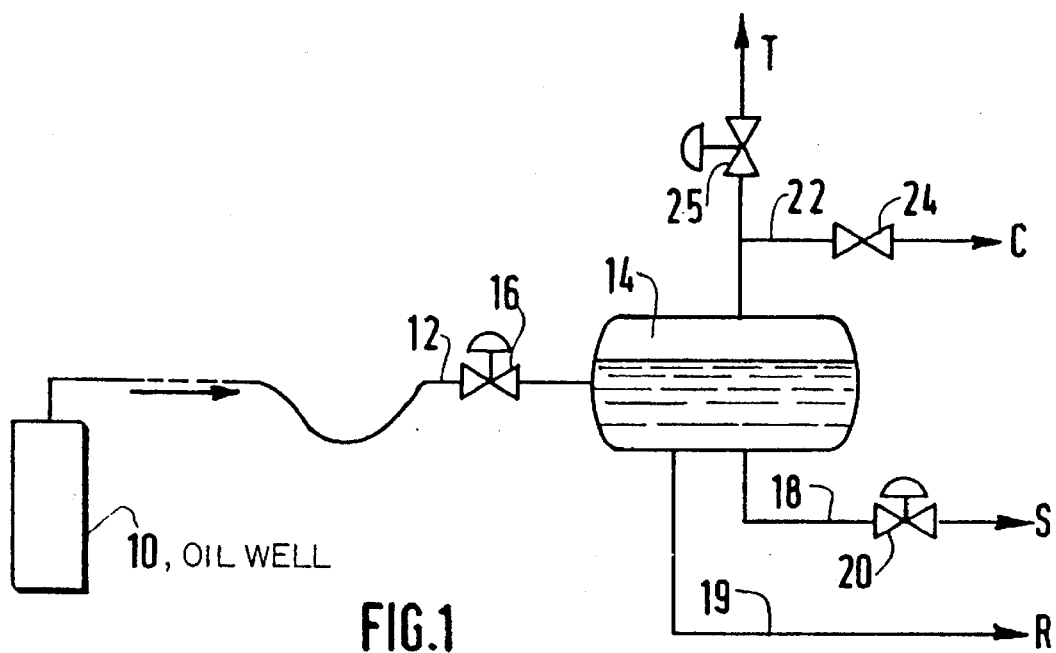
FIG. 1 illustrates diagrammatically a hydrocarbon transport system running from a production well to treatment equipment.

The system illustrated in FIG. 1 includes an oil well 10, for example an undersea well, from which the multiphase fluid is circulated through a steel pipeline 12 to treatment units on the coast. These units incorporate a separation tank 14 in which the fluid is held before undergoing decantation. The tank intake is controlled by an intake valve 16. After decantation, the oil and water are drawn off at the bottom of the tank by two pipes 18 and 19. The oil is circulated through a valve 20 to separation and treatment stations S located downstream in the system, and the water is treated before being returned to the sea or reinjected at R. The gaseous phase is fed to a compressor C through a pipe 22 regulated by a valve 24. In the event of excess gas in the tank, a portion of the gas is diverted through a valve 25 to a surplus gas burner T, where it is burned.

Figure 2:
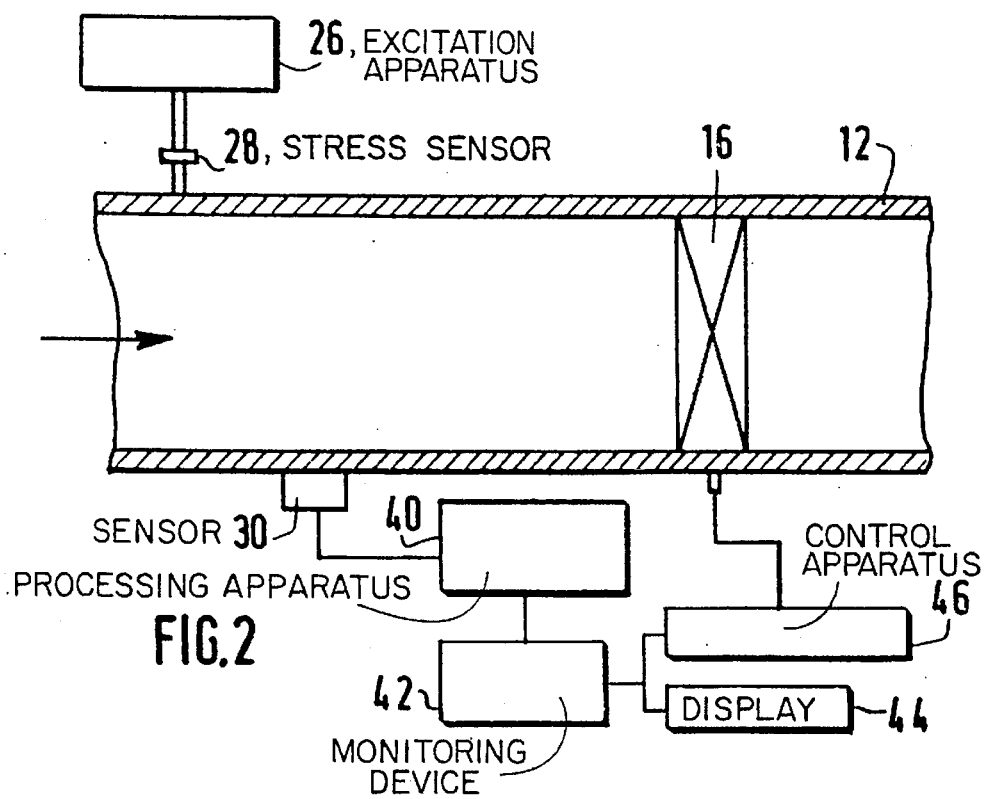
FIG. 2 is a diagrammatic cross-sectional view of a pipeline used to transport a multiphase fluid and of a device employed in a measurement area according to the invention.

To optimize the operation of the petroleum equipment and, in particular, to avoid oversizing it, use is made, according to the invention, of the flow rate-measurement and control apparatus shown in FIG. 2. This figure illustrates a section of pipeline 12 located upstream from the separation tank 14.

The apparatus according to the invention includes one excitation apparatus 26 for each measurement area, for generating and applying vibratory and acoustic excitation to the pipeline. FIG. 2 shows only one excitation apparatus corresponding to one measurement area. The excitation apparatus may be supplied with electrical, pneumatic, or hydraulic power. It may consist of an impact separator, a vibrating can, or ceramic piezoelectric pellets.

The excitation apparatus 26 generates vibratory excitation at one point on the outer surface of the pipeline. A strain gauge or stress sensor 28 is provided to check the proper energy and frequency related operation of the excitation apparatus.

Arranged on the outside of the pipeline 12, in proximity to the excitation apparatus, is at least one sensor 30, which collects vibration and acoustic data supplied to it through the pipeline. These data are transformed into electric signals characterizing the properties of the pipeline and the multiphase fluid being transported. Accordingly, these signals allow instantaneous analysis of the composition of the fluid flowing at a right angle to the sensor and, in particular, the presence of gas pockets or liquid plugs in the fluid.

The sensors distinguish between gas pockets and liquid plugs based on the different acoustic transmission characteristics of gases and liquids. Resonance frequency is inversely proportional to density, and gas has a higher resonance frequency than liquid. Thus, vibratory energy (i.e., resonance frequency) recorded by the sensor decreases after a tail of an air pocket passes through the pipeline. This decrease in vibratory energy is illustrated in the strip chart record of FIG. 3 by spaces 34 and 36. Succinctly put, a sudden increase in vibratory energy detected by the sensors indicates the presence of gas in the pipeline, and a subsequent decrease in vibratory energy indicates the tail end of the gas pocket, and thus the existence of liquid.

Figure 3:
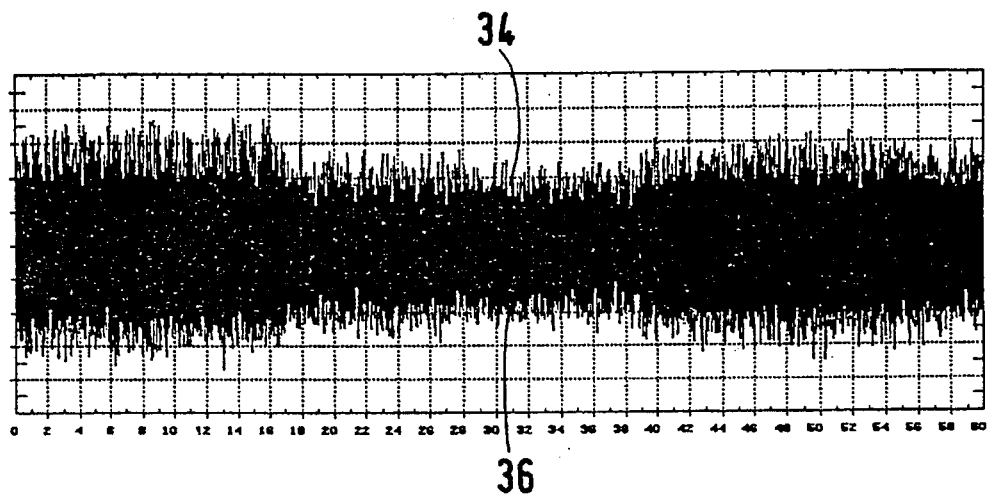
FIG. 3 shows an unprocessed signal captured by a sensor, before processing.
Figure 4:
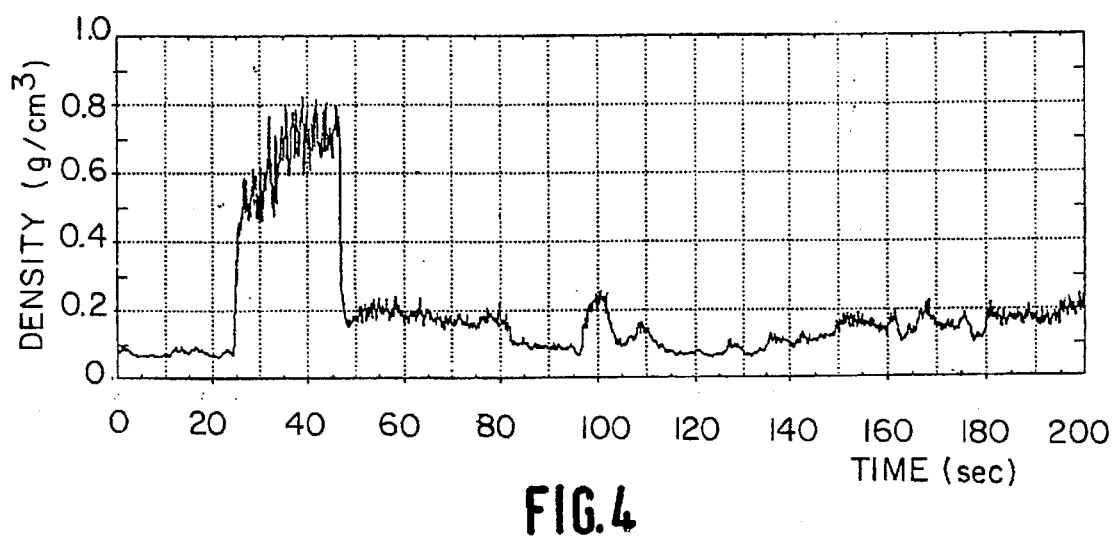
FIG. 4 shows a signal after processing.

Because the interpretation of the unprocessed signal in FIG. 3 is difficult, this signal is processed in a processing apparatus 40, which forms the reversed contour of the temporal signal and which filters the signal in order to remove interference. FIG. 4 illustrates an example of a processed signal.

The signal processed in this way enters a monitoring device 42, which transmits it to a display 44 and to a control apparatus 46. The control apparatus regulates the valves 16, 20, 24 (only valve 16 is shown in FIG. 2 to simplify the drawing), thereby adjusting the passage of the various phases of the effluent to the separation tank 14, to the compressor C, and to the separation and processing equipment S.

The length and speed characteristics of the liquid plugs and gas pockets are determined using a single vibration exciter and a minimum of two sensors placed along the length of the pipeline. More specifically, the successive passages of the fronts and the tails of the liquid plugs and gas pockets are detected by the sensors using resonance frequency measurements, as explained above. Then, the time differences between receipt of acoustic signals by each of the sensors may be determined, and thus the length and speed characteristics of the liquid plugs and gas pockets.

The invention makes it possible, using non-intrusive and non-radioactive measurements, to determine the quantities of delivered liquid and gas contained in a multiphase fluid, by measuring the length and velocity of the liquid plugs and gas pockets formed in this fluid.

We claim:

1. A method for the non-intrusive measurement and control of flow rates of gaseous and liquid phases in a multiphase fluid circulating in a pipeline between an oil well and a separation tank in which said gaseous and liquid phases are separated and conveyed to respective treatment equipment, said method comprising the steps of:

a) mechanically exciting the pipeline and the multiphase fluid contained therein by generating, in at least two areas of the outer surface of the pipeline located upstream from said separation tank, a vibratory or acoustic excitation, each excited area constituting a measurement area, b) recording mechanical vibrations transmitted by the pipeline at at least one point lying outside the pipeline, c) processing and analyzing said vibrations to derive therefrom data representing a presence of at least one of gas pockets and liquid plugs in the multiphase fluid, including the length and speed of travel of said liquid plugs and gas pockets, and d) regulating, based on said data, intake flow rates of the gaseous and liquid phases in said separation tank and treatment equipment in order not to exceed the treatment or storage capacity thereof.

2. An apparatus for the non-intrusive measurement and control of flow rates of gaseous and liquid phases in a multiphase fluid circulating in a pipeline between an oil well and a separation tank in which said gaseous and liquid phases are separated and conveyed to respective treatment equipment, said apparatus comprising:

a) at least two mechanical or acoustic excitation apparatuses individually disposed externally to the pipeline for generating and applying mechanical vibrations to said pipeline in at least two areas of the outer surface thereof, said excitation apparatuses being mounted upstream from said separation tank, b) at least one sensor for each area, said sensor being positioned in proximity to said pipeline and on the outside thereof for detecting at least one of mechanical and acoustic data transmitted thereto along said pipeline from said excitation apparatus, c) processing and analysis equipment for deriving from said at least one of mechanical and acoustic data information regarding the gas and liquid content of the multiphase fluid, including the length and rate of travel of at least one of liquid plugs and air pockets, and d) a monitoring apparatus for controlling intake valves of said separation tank and treatment equipment to regulate the intake flow rate of the phases in accordance with the storage or treatment capacity thereof.

3. An apparatus according to claim 2, further comprising a strain gauge or stress sensor for measuring the intensity and frequency of vibrations emitted by said excitation apparatus.

* * * * *